(12) United States Patent
Mauro

(10) Patent No.: US 12,614,199 B2
(45) Date of Patent: Apr. 28, 2026

(54) MOTORIZED LIFTING AND TRANSFER CHAIR

(71) Applicant: Edward Mauro, Oldsmar, FL (US)

(72) Inventor: Edward Mauro, Oldsmar, FL (US)

( * ) Notice: Subject to any disclaimer, the term of this patent is extended or adjusted under 35 U.S.C. 154(b) by 833 days.

(21) Appl. No.: 17/958,650

(22) Filed: Oct. 3, 2022

(65) Prior Publication Data

US 2023/0028164 A1     Jan. 26, 2023

Related U.S. Application Data

(60) Provisional application No. 63/253,322, filed on Oct. 7, 2021.

(51) Int. Cl.
| | |
|---|---|
| *A61G 5/10* | (2006.01) |
| *A61G 5/04* | (2013.01) |
| *A61G 5/12* | (2006.01) |
| *A61G 5/14* | (2006.01) |
| *G06Q 10/06* | (2023.01) |
| *G06Q 10/0637* | (2023.01) |

(Continued)

(52) U.S. Cl.
CPC ........... *G06Q 30/0201* (2013.01); *A61G 5/04* (2013.01); *A61G 5/1002* (2013.01); *A61G 5/104* (2013.01); *A61G 5/1094* (2016.11); *A61G 5/124* (2016.11); *A61G 5/128* (2016.11); *A61G 5/14* (2013.01); *G06Q 10/06* (2013.01); *G06Q 10/0637* (2013.01); *G06Q 10/06375* (2013.01); *G06Q 30/02* (2013.01); *G06Q 50/16* (2013.01); *A61M 5/1417* (2013.01)

(58) Field of Classification Search
CPC . A61G 5/04; A61G 5/14; A61G 5/124; A61G 5/1094; A61G 5/1002
See application file for complete search history.

(56) References Cited

U.S. PATENT DOCUMENTS

| | | | |
|---|---|---|---|
| 5,161,812 A | 11/1992 | Deweese | |
| 5,944,338 A * | 8/1999 | Simpson .............. | A61G 5/1094 280/47.38 |

(Continued)

FOREIGN PATENT DOCUMENTS

| | | | | |
|---|---|---|---|---|
| CA | 2862657 | 6/2017 | | |
| CN | 113018009 A * | 6/2021 | ........... | A61G 5/1059 |

(Continued)

*Primary Examiner* — Matthew Troutman
*Assistant Examiner* — Alison N Labarge
(74) *Attorney, Agent, or Firm* — ALLEN, DYER, DOPPELT + GILCHRIST, P.A

(57) ABSTRACT

A motorized lifting and transfer chair includes a base having a front portion and an opposing rear portion, where the rear portion has a pair of foot rests. The chair also includes a plurality of wheels mounted to the base configured to be selectively locked, and a vertical post assembly secured proximate to the rear portion of the base and extending upwards from the base. In addition, the chair includes a seating platform cantilevered from the vertical post assembly, where the seating platform comprises two portions with an aperture formed along two adjacent edges of the two portions and the two portions are configured to swing open and closed about the vertical post assembly. The chair includes a motorized device that raises and lowers the seating platform, and a latch is configured to secure the two portions of the seating platform closed.

17 Claims, 9 Drawing Sheets

(51) Int. Cl.
    *G06Q 30/02*       (2023.01)
    *G06Q 30/0201*    (2023.01)
    *G06Q 50/16*       (2012.01)
    *A61M 5/14*        (2006.01)

(56)                 References Cited

U.S. PATENT DOCUMENTS

| | | |
|---|---|---|
| 7,690,055 B2 | 4/2010 | Hammer et al. |
| 9,579,001 B2 | 2/2017 | Ahmed |
| 2004/0049841 A1 | 3/2004 | Brotherston et al. |
| 2007/0118990 A1* | 5/2007 | Kuenzel ............... A61G 5/1002 |
| | | 5/618 |
| 2014/0306495 A1 | 10/2014 | Griggs et al. |
| 2018/0271335 A1 | 9/2018 | Hart et al. |
| 2021/0290459 A1* | 9/2021 | Glikman .............. A61G 5/1059 |
| 2025/0000731 A1* | 1/2025 | Lin ...................... A61G 7/1088 |

FOREIGN PATENT DOCUMENTS

| | | | | |
|---|---|---|---|---|
| JP | 2018023752 A | * | 2/2018 | |
| KR | 102214760 B1 | * | 2/2021 | ............. A61G 5/124 |
| WO | WO2014120274 | | 8/2014 | |
| WO | WO-2021072911 A1 | * | 4/2021 | ........... A61G 5/0808 |

* cited by examiner

MOTORIZED LIFTING AND TRANSFER CHAIR

RELATED APPLICATION

This application claims priority to U.S. Provisional Application Ser. No. 63/253,322 filed on Oct. 7, 2021 the contents of which are herein incorporated by reference in their entirety.

FIELD

The present invention relates to the field of wheelchairs, and, more particularly, to a motorized accessory lifting and transfer chair.

BACKGROUND

Handicap and disabled persons require assistance in moving to and from the toilet. This typically requires a nurse or other similar type of personnel to physically lift and move the person from a wheelchair to the toilet seat. It is an awkward process and subject to causing injury during the move to both the nurse and the disabled person.

Accordingly, there is a need in the art for a transfer device that allows the easy transition from a wheelchair or bed to the toilet.

SUMMARY

In view of the foregoing background, it is therefore an object of the present invention to provide a transfer device that is easy to operate and efficient to move a disabled person with little physical effort. This and other objects, features, and advantages in accordance with the present invention are provided by a motorized lifting and transfer chair.

The chair includes a base having a front portion and an opposing rear portion, a plurality of wheels mounted to the base, a vertical post assembly secured proximate to the rear portion of the base and extending upwards from the base, and a seating assembly comprising a seating platform cantilevered from the vertical post assembly. The seating platform comprises two portions with an aperture formed along two adjacent edges of the two portions and the two portions are configured to swing open and closed about the vertical post assembly. A motorized device raises and lowers the seating platform.

The motorized lifting and transfer chair may also include a latch configured to secure the two portions of the seating platform closed, and where the seating assembly further comprises an upper crossbeam and a push bar. The base may have two opposing beams that are parallel to each other and a lower crossbeam therebetween. The motorized device may include a linear actuator secured between the upper crossbeam of the seating assembly and the lower crossbeam of the base and be configured to raise and lower the seating platform.

The rear portion of the base may have a pair of foot rests for a patient, and the vertical post assembly may include an intravenous (IV) bag holder. In addition, the chair may include a tray removably secured to the seating assembly. The plurality of wheels may be configured to be selectively locked so that the chair does not roll. The chair may also have a cushion carried by the seating platform, and the motorized device may have a rechargeable battery and a charging port for charging the rechargeable battery.

In another aspect a method of using a motorized lifting and transfer chair comprising a base having a front portion and an opposing rear portion, a vertical post assembly secured proximate to the rear portion of the base and extending upwards from the base, a seating assembly comprising a seating platform having two separate portions cantilevered from the vertical post assembly and configured to swing open and closed about the vertical post assembly, and a motorized device that raises and lowers the seating platform, is disclosed. The method includes swinging open the seating platform to separate the two portions of the seating platform to load a patient, loading the patient on to the seating platform, and swinging closed the two portions of the seating platform after the patient is loaded thereon in a sitting position. The method also includes raising the seating platform along with the patient using the motorized device, rolling the motorized lifting and transfer chair to a desired location, and lowering the seating platform along with the patient to a desired height. In addition, the method may include latching the seating platform closed after the patient is loaded on to the seating platform.

BRIEF DESCRIPTION OF THE DRAWINGS

The aspects and the attendant advantages of the embodiments described herein will become more readily apparent by reference to the following detailed description when taken in conjunction with the accompanying drawings wherein.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

More than 33% of people over the age of sixty-five have a slip and fall accident each year. In addition, injuries getting on and off the toilet are high in people sixty-five or older, with individuals over eighty-five suffering more than half of their injuries near the toilet. For example, injuries occupying while getting on and off the toilet increase with age, starting at 19.3% for people over sixty-five, reaching 36.9% for individuals over eighty-five.

Figure 1:
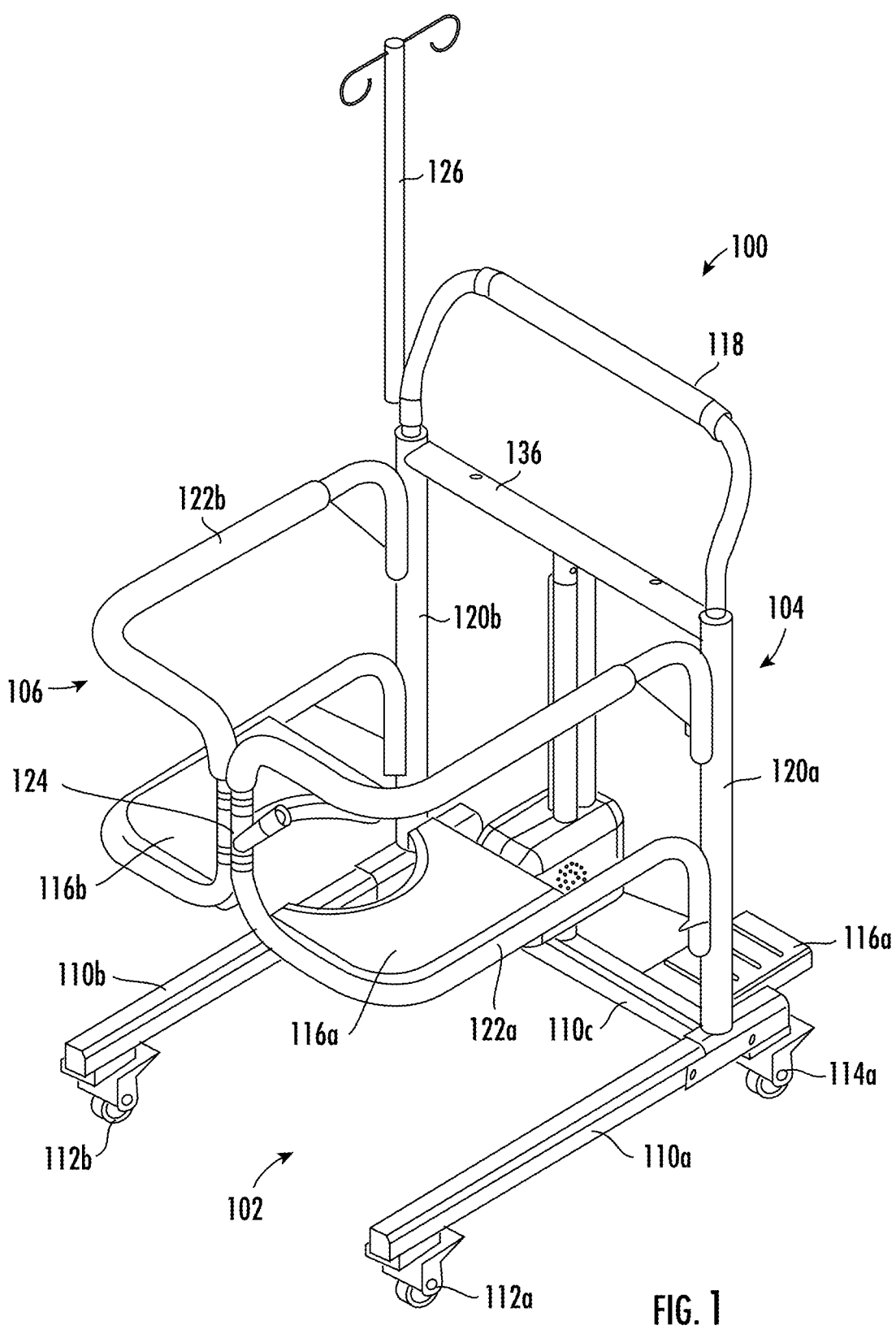
FIG. 1 is a right side perspective view of a motorized lifting and transfer chair in accordance with the present disclosure.
Figure 2:
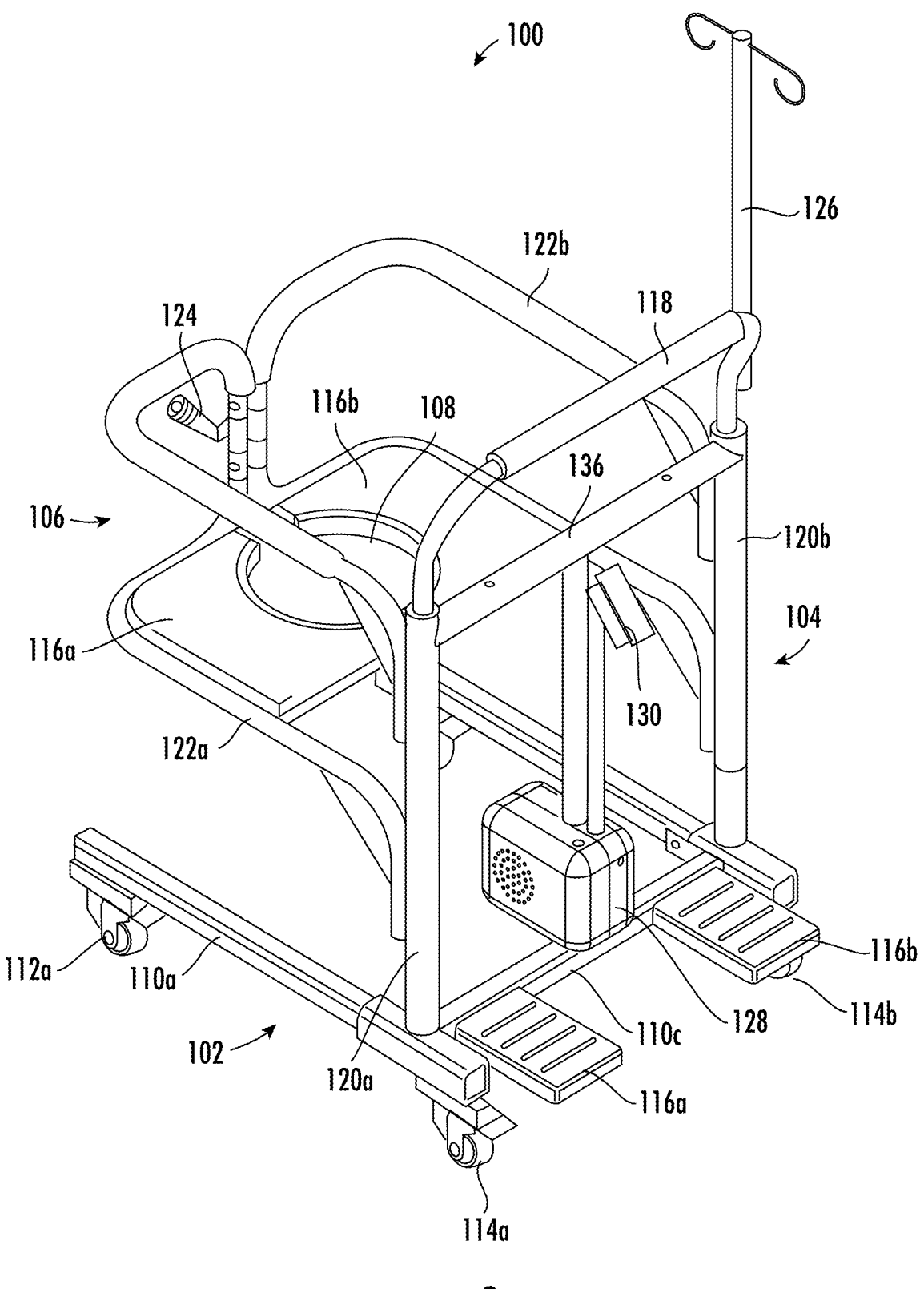
FIG. 2 is a left side perspective view of the chair.

A motorized lifting and transfer chair of the invention chair 100 is designed for transporting mobility-disabled persons from bed, or wherever they may be seated, to the bathroom without having to stand or use physical strength to get there. Referring to FIGS. 1 and 2, the motorized lifting and transfer chair of the invention is shown. The chair 100 is configured to lift over four hundred pounds and may include a removable intravenous (IV) drip bag holder 126 and a rechargeable long lasting battery as discussed below. The lifting and transfer chair 100 includes a base 102 and a plurality of wheels mounted to the base 102. The plurality of wheels includes a set of front wheels 112a and a set of rear wheels 114a, 114b. The wheels can rotate 360 degrees to make the chair 100 easy to maneuver in tight spaces. In addition, the wheels 112a, 112b, 114a, 114b can be locked in place to prevent the chair 100 from moving when loading or unloading a patient from the chair 100, for example.

The base 102 is configured to support the weight of the patient and is comprised of metal such as steel or aluminum. The base 102 may be comprised of a first beam 110a on a right side of the chair 100 and a second beam 110b on the left side of the chair 100. The first and second beams 110a, 110b are spaced apart from each other and are typically parallel to one another with a lower crossbeam 110c therebetween. The beams 110a, 110b are positioned to be able to slide under a bed as a patient is being loaded into the chair from the bed.

A vertical post assembly 104 is secured proximate to a rear portion of the base 102 and extends upwards from the base 102. A seating assembly 106 is secured to the vertical post assembly 104 and includes a seating platform 115 comprising two portions 116a, 116b. The seating assembly 106 includes a gate framework 122a, 122b for the respective portions 116a, 116b of the seating platform 115. The gate framework 122a, 122b slidingly engages the vertical post assembly 106.

The two portions 116a, 116b are cantilevered out from the vertical post assembly 104 and form an aperture 108 along two adjacent edges of the two portions 116a, 116b. Each of the two portions 116a, 116b are configured to move independently to swing open and closed about the vertical post assembly 104. A latch 124 at a front of the seating assembly 106 is used to secure the two portions 116a, 116b of the seating platform 115 closed.

In addition, a motorized device 128 is mounted to an upper crossbeam 136 of the seating assembly 106 and is activated using a controller 130. When the motorized device 128 is activated, it moves the seating platform 115 vertically relative to the vertical post assembly 104 as the seating assembly 106 is raised or lowered. The motorized device 128 may comprise a linear actuator as those of ordinary skill in the art can appreciate. Vertical downtubes 120a, 120b of the seating assembly 106 slidingly engage the vertical post assembly 104 concentrically which allows movement vertically. The framework 122a, 122b is hingedly coupled to the vertical downtubes 120a, 120b, which allow rotational movement of the seating platform portions 116a, 116b relative to the vertical post assembly 104.

A push bar 118 is positioned above the upper cross beam 136 and will raise and lower together with the seat assembly 106. The push bar 118 is configured to be used by a care giver to maneuver the chair 100.

Figure 3:
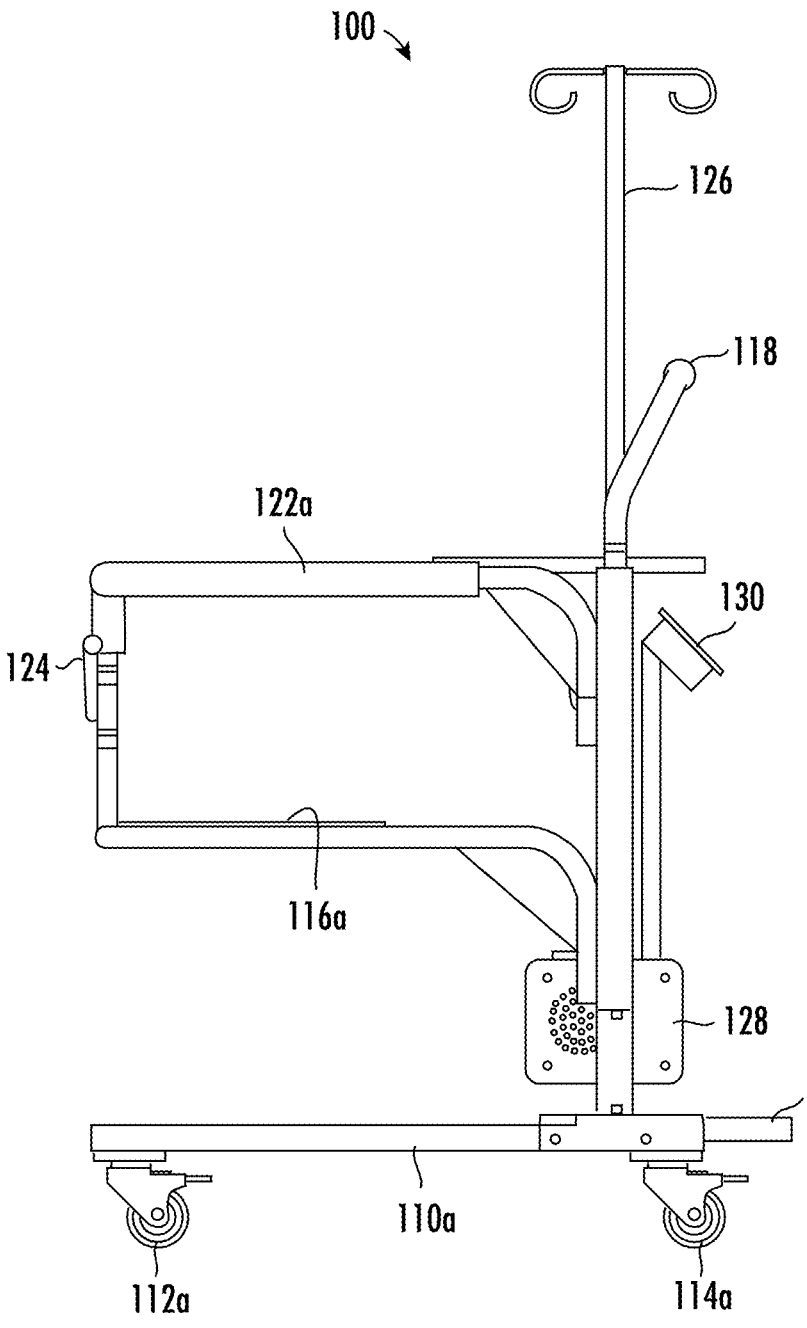
FIG. 3 is a right side elevational view of the chair.
Figure 4:
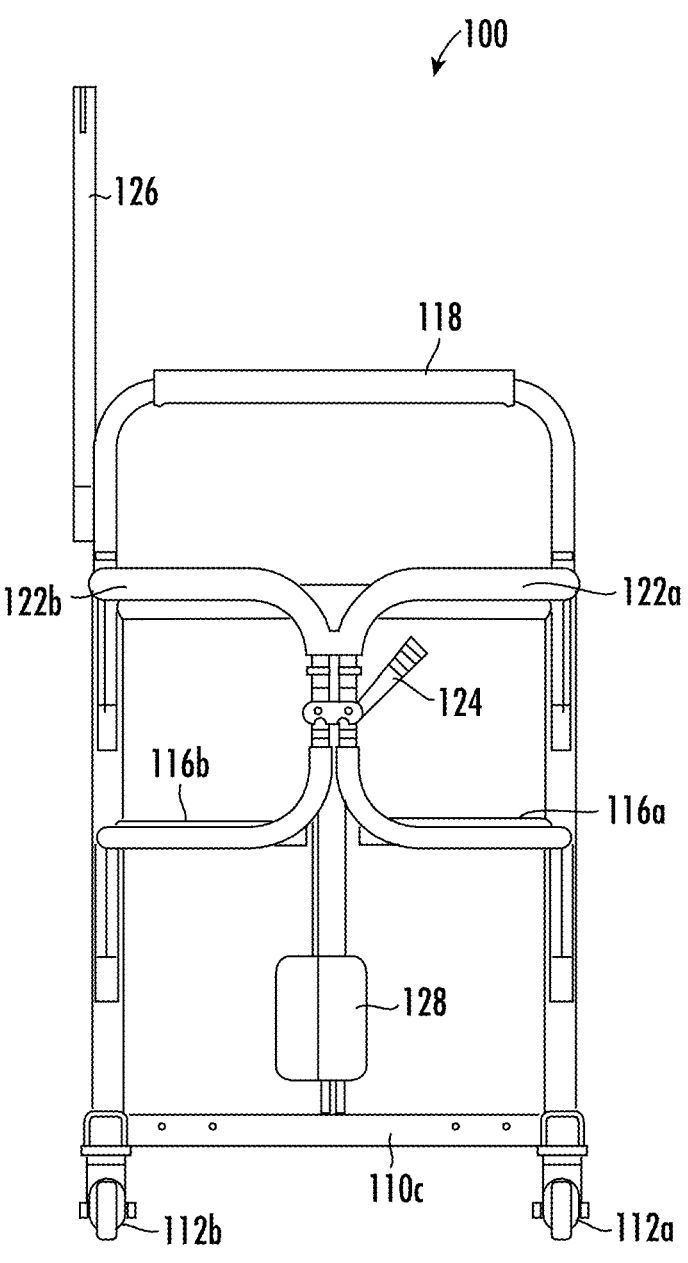
FIG. 4 is a front elevational view of the chair.

Referring now to FIGS. 3 and 4, the right side elevational view and front view of the lifting and transfer chair 100 is shown, respectively. The gate framework 122a includes upper and lower rails that are used to secure the patient on the seating platform 115. The rear of the gate framework

122a, 122b may serve as a back rest for the patient and the patient can place their feet on the foot rests 116a, 116b. The latch 124 is located on the outside of the gate framework 122a, 122b.

Figure 5:
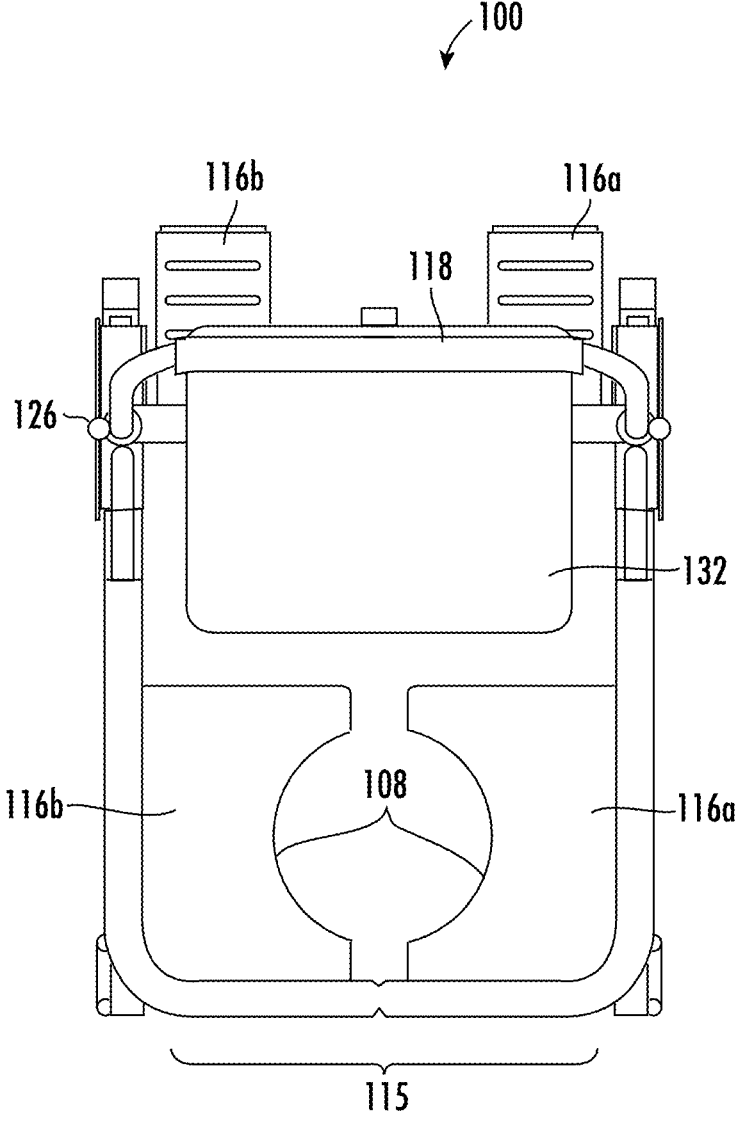
FIG. 5 is a top view of the motorized lifting and transfer chair.

As best seen on FIG. 5, the seating platform 115 includes two portions 116a, 116b that form an aperture 108 along two adjacent edges. The aperture 108 can be used by the patient for toileting purposes when the seating platform 115 is positioned and lowered over a toilet.

Figure 6:
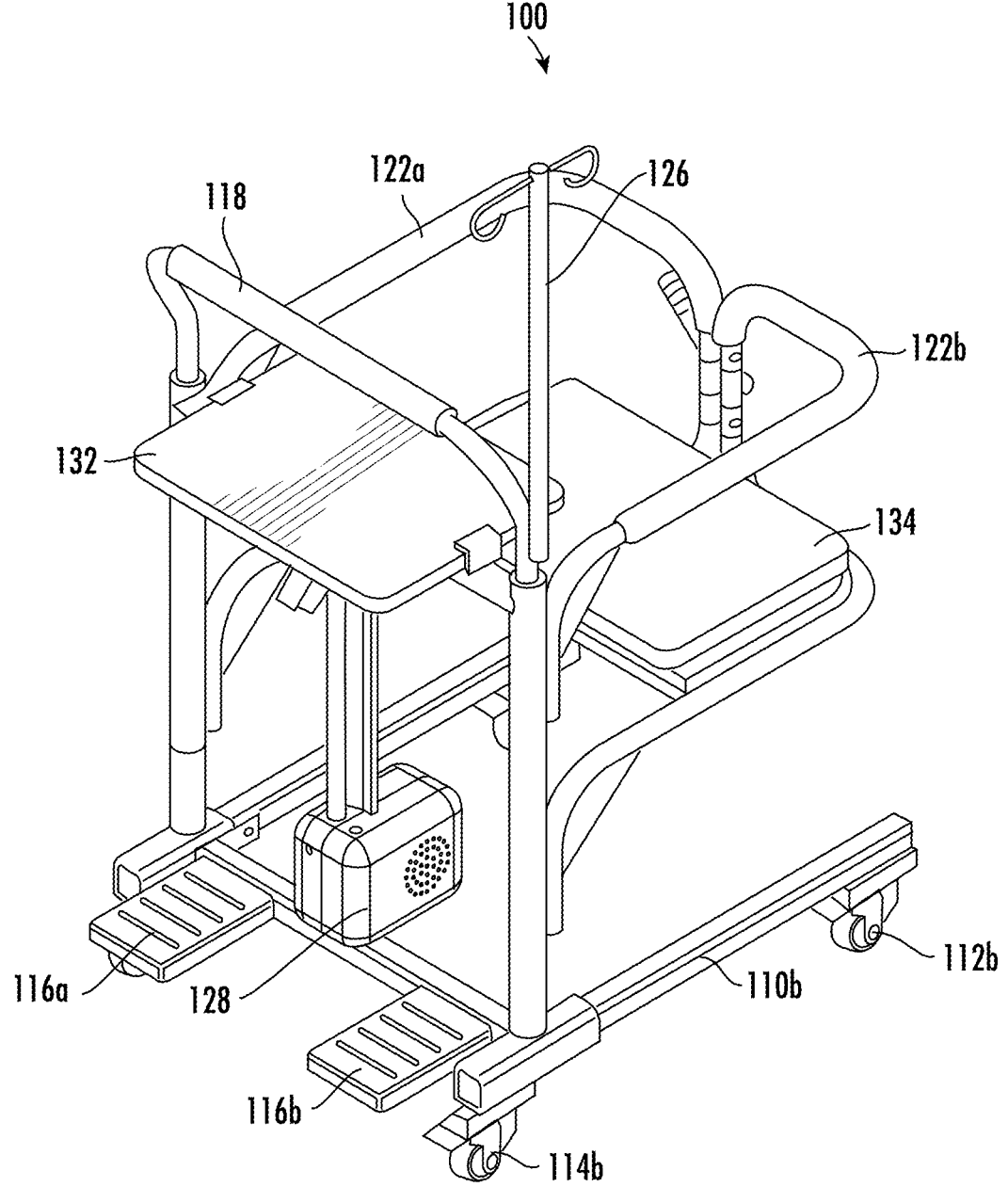
FIG. 6 is a rear perspective view of the chair.

The lifting and transfer chair 100 may also include a tray 132 removably secured to the vertical post assembly 104 as shown in FIG. 6. The chair 100 may also include a seating cushion 134 that can be placed on the seating platform 115. The motorized device 128 may comprise a linear actuator that is secured between the upper crossbeam 136 of the seating assembly 106 and the lower crossbeam 110c of the base 102 and the linear actuator is configured to raise and lower the seating assembly 106.

The lifting and transfer chair 100 may be twenty-five inches wide and can support four hundred twenty-five pounds. The motorized device 128 may have a 96W electric motor to drive the linear actuator and a twelve to fifteen battery life for a rechargeable lithium battery. The plurality of wheels 112a, 112b, 114a, 114b may comprise 360 degree castors.

Figures 7, 8:
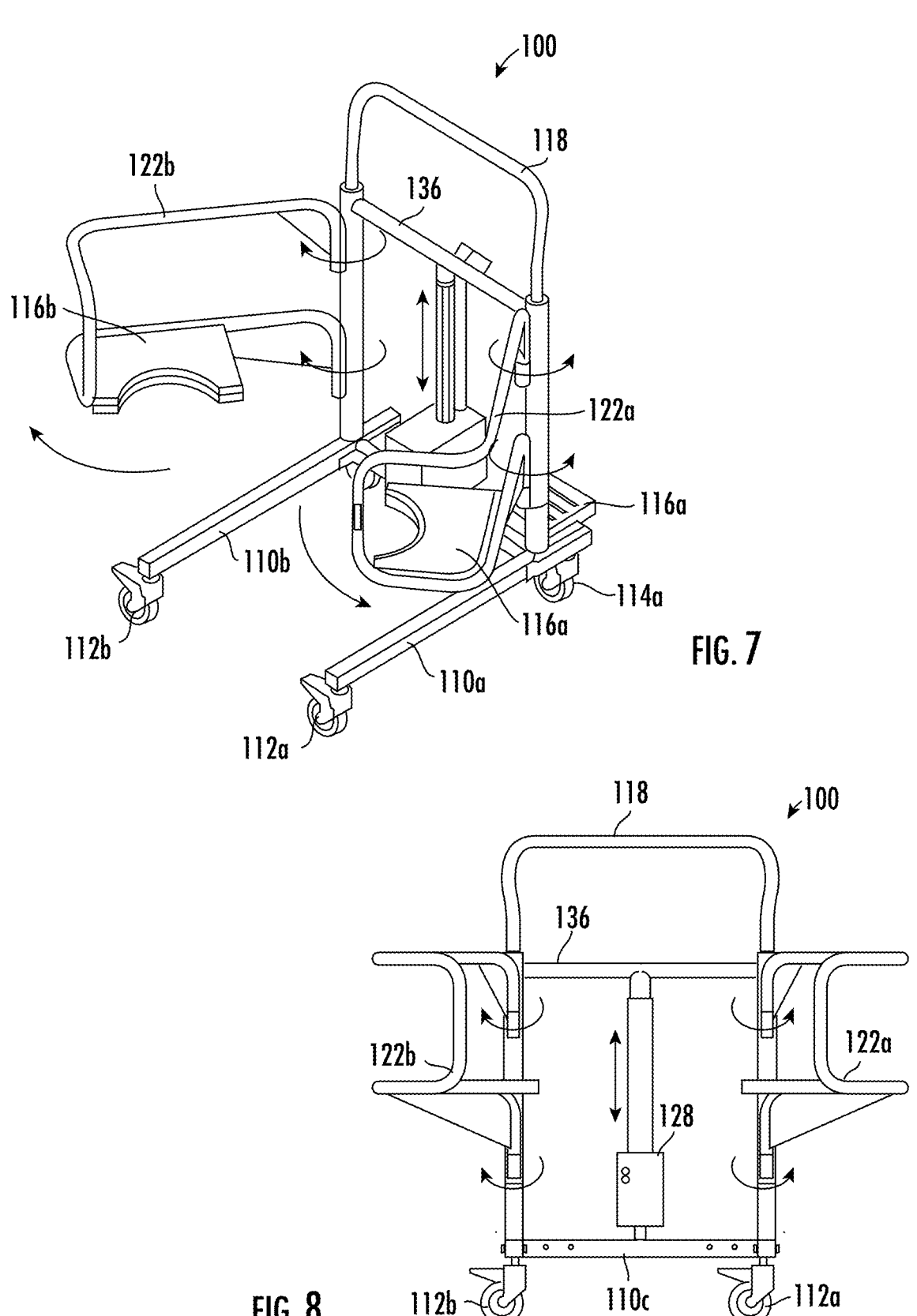
FIG. 7 is a perspective view of the chair showing a seating platform in the open position.
FIG. 8 is a front view of the chair of FIG. 7 with the seating platform in the open position.

In operation, the frame and seating portion is moved to an open position as shown in FIGS. 7 and 8. The chair 100 is pushed forward around a person sitting on a bed, for example. The seating platform 115 is then slid under the person and closed so that the person is now sitting on the seating platform 115. The seating platform 115 is lifted using the motorized device 128 so that the person is raised off the bed surface.

The chair 100 can then be rolled to the new location. For example, the chair 100 can be rolled over to a toilet and either lower the person onto the toilet seat or hold the person just above. The chair 100 can be rolled over to a piece of furniture and the person can be lowered down until the seating platform 115 is on the surface of the furniture. The seating platform 115 can be opened so that the person is now sitting on the furniture. The chair 100 can then be pulled back and away from the person. The seating platform 115 can be lowered to about nineteen inches from a ground surface and can be raised to about twenty-nine inches from the ground surface. This provides about ten inches of lifting distance.

Figure 9:
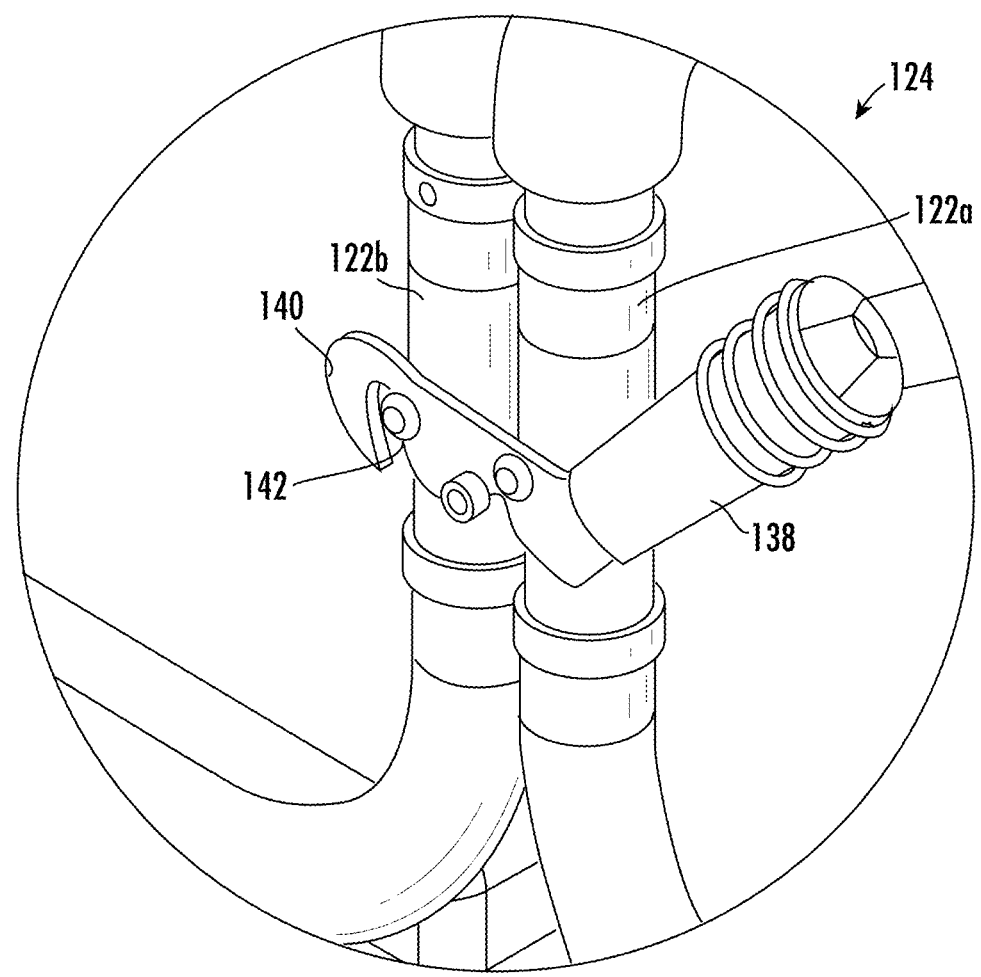
FIG. 9 is a detail view of a latch of the chair used to secure the seating platform in the closed position.

A detail view of the latch 124 is shown in FIG. 9. The latch 124 includes a handle 138 coupled to a latch arm 140. The handle 138 is used to raise and lower the latch arm 140 over a catch 142 that secures the gate framework 122a, 122b closed.

Figure 10:
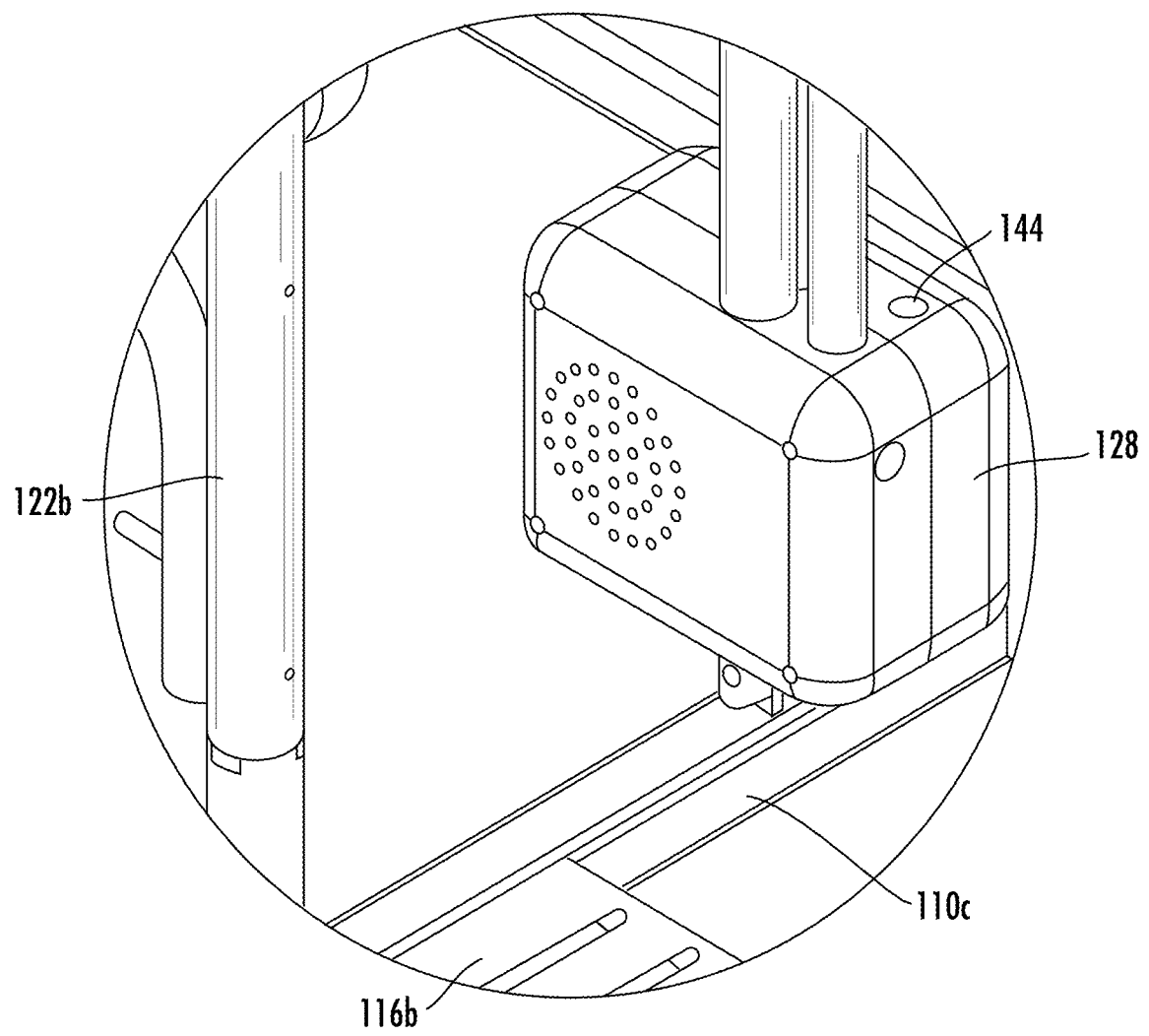
FIG. 10 is a detail view of a portion of a motorized device of the chair used to raise and lower the seating platform.

A detail view of a portion of the motorized device 128 is shown in FIG. 10. As discussed above, the motorized device 128 is powered by a rechargeable battery and includes a charging port 144. The motorized device 128 is used to raise and lower the seating assembly 106.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A motorized lifting and transfer chair comprising:
   a base having a front portion and an opposing rear portion;

5 a plurality of wheels mounted to the base;

a pair of vertical pivot posts positioned toward the rear portion of the base and extending upward therefrom;

a seating platform comprising two portions respectively pivotably coupled to the pair of vertical pivot posts, the two portions being configured to swing open and closed about the vertical pivot posts and defining a central aperture between opposing inner edges of the two portions;

armrests disposed on opposite sides of the seating platform;

a motorized device positioned between the pair of pivot posts and being configured to move vertically to raise and lower the seating platform;

an upper crossbeam extending between the pair of pivot posts, the upper crossbeam positioned approximately at the same height as the armrests and configured to move vertically in unison with the armrests and the seating platform;

a push bar positioned above the upper cross beam at the rear portion of the base for pushing and maneuvering the chair by an operator while face to face with a patient seated in the chair; and wherein the chair is configured to be pushed using the push bar to allow the chair to be rolled over a toilet or bed while the patient remains seated.

2. The motorized lifting and transfer chair of claim 1, further comprising a latch configured to secure the two portions of the seating platform closed.

3. The motorized lifting and transfer chair of claim 2, wherein the base comprises two opposing beams that are parallel to each other and a lower crossbeam therebetween.

4. The motorized lifting and transfer chair of claim 3, wherein the motorized device comprises a linear actuator.

5. The motorized lifting and transfer chair of claim 1, wherein the rear portion of the base has a pair of foot rests.

6. The motorized lifting and transfer chair of claim 1, further comprises an intravenous (IV) bag holder.

7. The motorized lifting and transfer chair of claim 1, further comprising a tray.

8. The motorized lifting and transfer chair of claim 1, wherein the plurality of wheels are configured to be selectively locked.

9. The motorized lifting and transfer chair of claim 1, further comprising a cushion carried by the seating platform.

10. The motorized lifting and transfer chair of claim 1, wherein the motorized device comprises a rechargeable battery and a charging port for charging the rechargeable battery.

11. A motorized lifting and transfer chair comprising:

a base having a front portion and an opposing rear portion, wherein the rear portion having a pair of foot rests;

a plurality of wheels mounted to the base configured to be selectively locked;

a pair of vertical pivot posts positioned toward the rear portion of the base and extending upward therefrom;

a seating platform comprising two portions respectively pivotably coupled to the pair of vertical pivot posts, the two portions being configured to swing open and closed about the vertical pivot posts and defining a central aperture between opposing inner edges of the two portions;

armrests disposed on opposite sides of the seating platform;

a motorized device that raises and lowers the seating platform;

an upper crossbeam extending between the pair of pivot posts, the upper crossbeam positioned approximately at the same height as the armrests and configured to move vertically in unison with the armrests and the seating platform;

a push bar positioned above the upper crossbeam at the rear portion of the base for pushing and maneuvering the chair by an operator while face to face with a patient seated in the chair; and a latch configured to secure the two portions of the seating platform closed;

wherein the chair is configured to be pushed using the push bar to allow the chair to be rolled forward over a toilet or bed while the patient remains seated.

12. The motorized lifting and transfer chair of claim 11, further comprises an intravenous (IV) bag holder.

13. The motorized lifting and transfer chair of claim 11, further comprising a tray removably secured to the motorized lifting and transfer chair.

14. The motorized lifting and transfer chair of claim 13, further comprising a cushion carried by the seating platform.

15. The motorized lifting and transfer chair of claim 11, wherein the motorized device comprises a rechargeable battery and a charging port for charging the rechargeable battery.

16. A method of using a motorized lifting and transfer chair comprising a base having a front portion and an opposing rear portion, a pair of vertical pivot posts positioned toward the rear portion of the base and extending upward therefrom, a seating platform having two separate portions pivotably coupled to the pair of vertical pivot posts and configured to swing open and closed about the vertical pivot posts, armrests disposed on opposite sides of the seating platform, and a motorized device positioned between the pair of pivot posts and configured to move vertically to raise and lower the seating platform, the method comprising:

swinging open the seating platform to separate the two portions of the seating platform to load a patient;

loading the patient on to the seating platform;

swinging closed the two portions of the seating platform after the patient is loaded thereon in a sitting position;

raising the seating platform along with the patient using the motorized device;

pushing the chair forward using a push bar positioned above an upper crossbeam at the rear portion of the base;

rolling the motorized lifting and transfer chair to a desired location by an operator while face to face with the patient seated in the chair; and lowering the seating platform along with the patient to a desired height;

wherein the chair is configured to be rolled forward over a toilet or bed while the patient remains seated.

17. The method of claim 16, further comprising latching the seating platform closed after the patient is loaded on to the seating platform.

* * * * *